(12) United States Patent
Riley et al.

(10) Patent No.: US 11,872,562 B1
(45) Date of Patent: Jan. 16, 2024

(54) CHEMICAL DETECTION TRAINING CONTAINER AND METHOD FOR USE THEREOF

(71) Applicant: U.S. Army Combat Capabilities Development Command, Chemical Biological Center, APG, MD (US)

(72) Inventors: Patrick C Riley, Bel Air, MD (US); Brian C Hauck, Baltimore, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 445 days.

(21) Appl. No.: 17/216,295

(22) Filed: Mar. 29, 2021

(51) Int. Cl.
*G01N 1/22* (2006.01)
*B01L 3/00* (2006.01)
*G09B 19/00* (2006.01)
*G01N 33/00* (2006.01)

(52) U.S. Cl.
CPC .............. *B01L 3/508* (2013.01); *G01N 1/22* (2013.01); *G09B 19/00* (2013.01); *B01L 2300/041* (2013.01); *B01L 2300/0858* (2013.01); *G01N 33/0004* (2013.01)

(58) Field of Classification Search
CPC ............ G09B 19/00; G01N 1/22; B01L 3/508
See application file for complete search history.

(56) References Cited

U.S. PATENT DOCUMENTS

| 3,012,956 | A | * | 12/1961 | Currier, Jr. | G21C 1/303 976/DIG. 35 |
| 4,927,605 | A | * | 5/1990 | Dorn | A61B 10/007 422/68.1 |
| 5,561,915 | A | * | 10/1996 | Vandergriff | F26B 21/14 141/10 |
| 2021/0187456 | A1 | * | 6/2021 | Corti | B01F 33/452 |
| 2021/0187457 | A1 | * | 6/2021 | Corti | B01F 33/86 |
| 2022/0266179 | A1 | * | 8/2022 | Yadav | F16H 57/0402 |

FOREIGN PATENT DOCUMENTS

| CN | 209260093 U | * | 8/2019 |
| CN | 212363727 U | * | 1/2021 |
| CN | 213456136 U | * | 6/2021 |
| CN | 219251122 U | * | 6/2023 |

\* cited by examiner

Primary Examiner — Jamel E Williams
(74) Attorney, Agent, or Firm — Ulysses John Biffoni

(57) ABSTRACT

A sealable sampling container includes a vessel having a bottom and walls upwardly extending therefrom and terminating in a sealing surface, the bottom and the walls defining a volume within the open top container. A gasket is configured to engage with the sealing surface of the vessel and a lid is configured to engage with the gasket at the sealing surface and lock to the vessel. A sampling port is affixed to one side of the vessel or the lid, the sampling port providing fluid communication between the volume within the open top container and an external environment. The sealable sampling container safely stores volatile chemical vapors and enables training on use of chemical detection equipment without resort to ventilation hoods or the use of respiratory protection equipment.

17 Claims, 6 Drawing Sheets

CHEMICAL DETECTION TRAINING CONTAINER AND METHOD FOR USE THEREOF

GOVERNMENT INTEREST

The invention described herein may be manufactured, used, and/or licensed by or for the United States Government.

FIELD OF THE INVENTION

The present invention relates in general to the technical field of chemical detection training equipment, and in particular to a sealable container for safely containing a sample of volatile vapors of a chemical while allowing a trainee to learn to use chemical detection equipment to sample the volatile vapors contained in the container for training purposes in an educational setting and without resort to ventilation hoods and in some instances personal protective equipment (PPE).

BACKGROUND OF THE INVENTION

Devices exist for sampling environments to test for the presence of chemical vapors and chemical fumes. The proper use of such chemical detection equipment is paramount to obtaining safe and accurate readings regarding the presence of chemical vapors and chemical fumes in a given environment. Accordingly, it is important that users of such chemical detection equipment receive proper training and adequate practice with the devices to enable proper use yielding safe and accurate readings.

Existing methods for vapor sampling within an educational environment have previously required ventilation devices such as a laboratory ventilation hood, also commonly known as a fume hood, to contain vapors and limit exposure thereto. Such fume hoods are large, require extensive engineering controls, and are immobile, thereby limiting chemical detection equipment training to designated classrooms and training facilities that must be specially equipped and maintained. The number of personnel able to be trained on the detection equipment are also limited by size and capacity of such designated training facilities and the number and size of fume hoods present in those designated training facilities and laboratories. Alternative options of fitting trainees with respirators and masks, self-contained breathing apparatus, or other forms of respiratory wear are even more cumbersome and impractical.

Thus, there exists a need for equipment that safely contains volatile chemical vapors to enable a trainee of chemical detection equipment to safely sample volatile vapors within any training setting as they are trained on the proper use and operation of chemical detection equipment while minimizing exposure of the user to the vapors contained within the training equipment.

SUMMARY OF THE INVENTION

The present invention provides a sealable sampling container for use with chemical detection equipment and in the education of a trainee of such equipment. The sealable sampling container includes a vessel having a bottom and a plurality of walls upwardly extending therefrom and terminating in a sealing surface, the bottom and the walls defining a volume. A gasket is configured to engage with the sealing surface of the vessel. A lid is configured to engage with the gasket at the sealing surface and lock to the vessel. A sampling port is affixed to one side of the vessel or the lid, the sampling port providing fluid communication between the volume within the vessel and an external environment. The sealable sampling container enables a trainee of chemical detection equipment to safely sample volatile vapors without the need for ventilation hoods or respiratory wear while being trained on the proper use and operation of chemical detection equipment and mitigating exposure of the trainee to sampled substances.

BRIEF DESCRIPTION OF THE DRAWINGS

The present invention is further detailed with respect to the following figures that depict various aspects of the present invention.

DETAILED DESCRIPTION OF THE PREFERRED EMBODIMENTS

The present invention has utility as a sealable container for safely containing a sample of volatile vapors of a chemical while allowing a trainee to learn to use chemical detection equipment to sample the volatile vapors contained in the container for training purposes in any training setting without the need for ventilation hoods or respiratory protection gear. The present invention enables a trainee of chemical detection equipment to safely sample volatile vapors within any training setting as they are trained on the proper use and operation of chemical detection equipment while minimizing exposure of the user to the vapors contained within the training equipment.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

As used herein, personal protective equipment is defined to include gloves, lab coats, protective suits and garments, goggles, masks, respirators, or combinations thereof.

Figure 1:
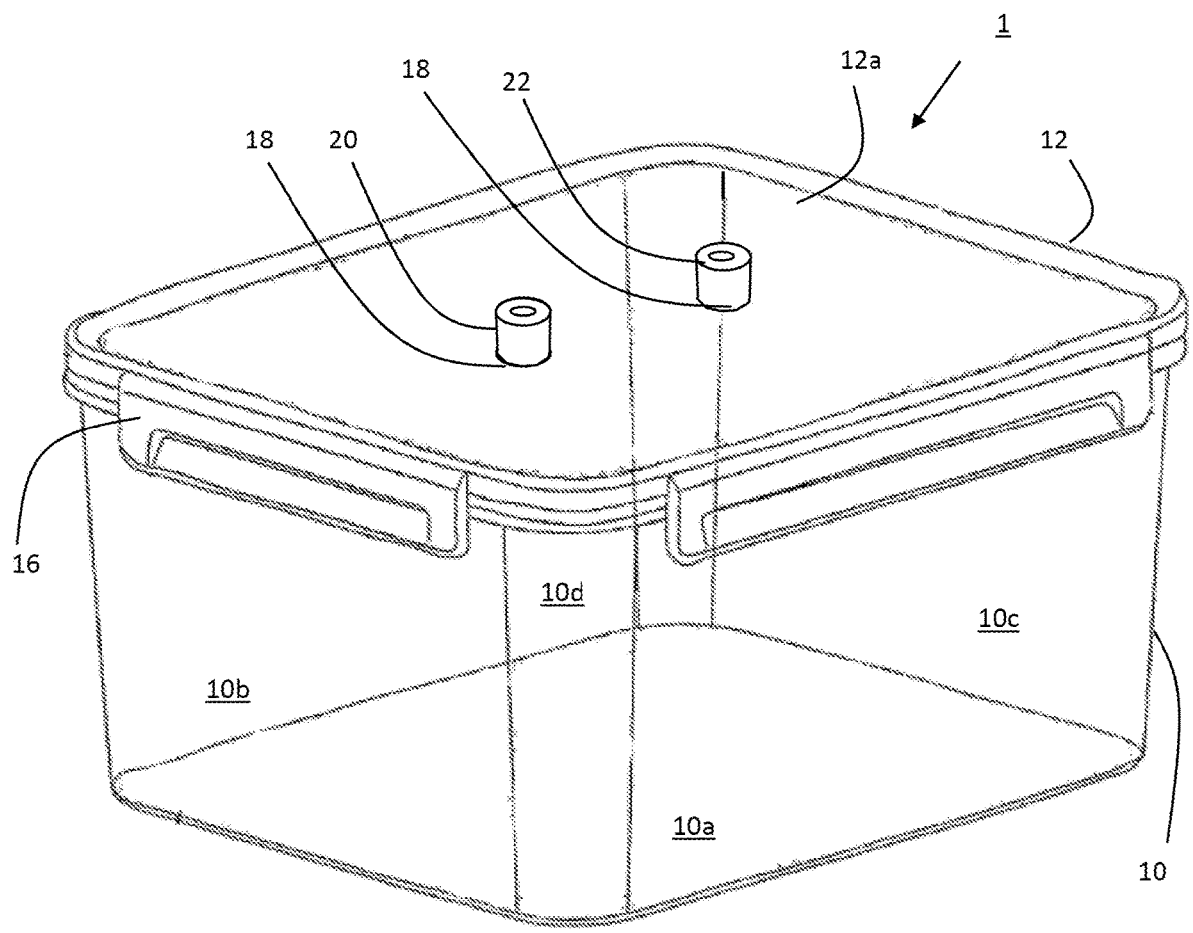
FIG. 1 is a perspective view of a sealable sampling container according to embodiments of the present invention with a lid in a closed position on a container.
Figure 2:
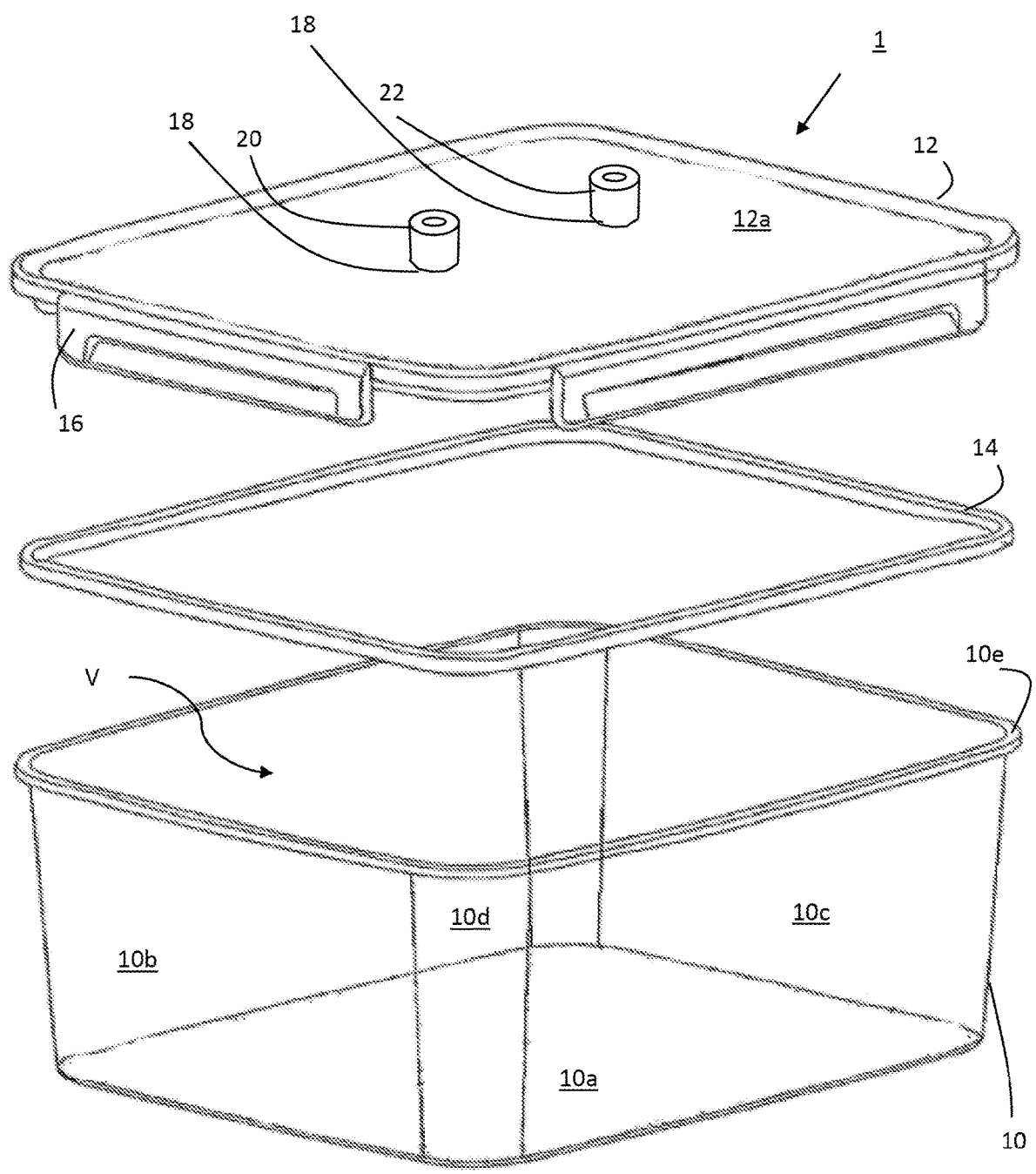
FIG. 2 is an exploded perspective view of a sealable sampling container according to embodiments of the present invention.
Figure 3:
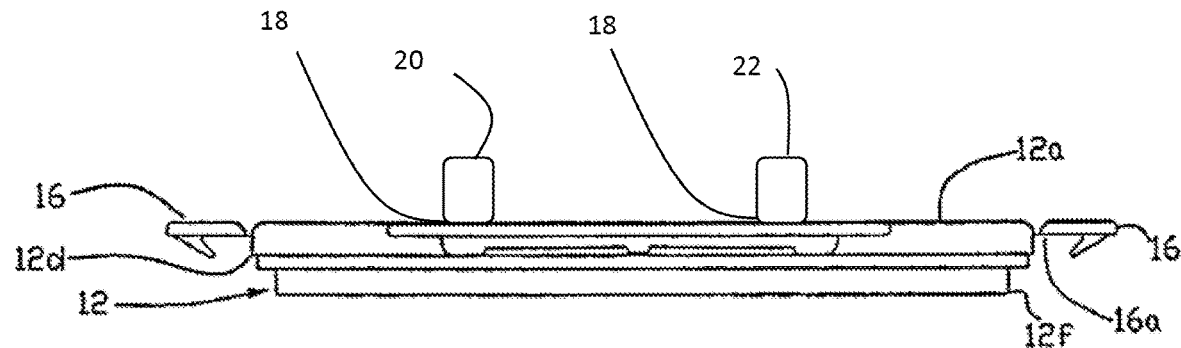
FIG. 3 is a side view of a lid of a sealable sampling container according to embodiments of the present invention.
Figure 6:
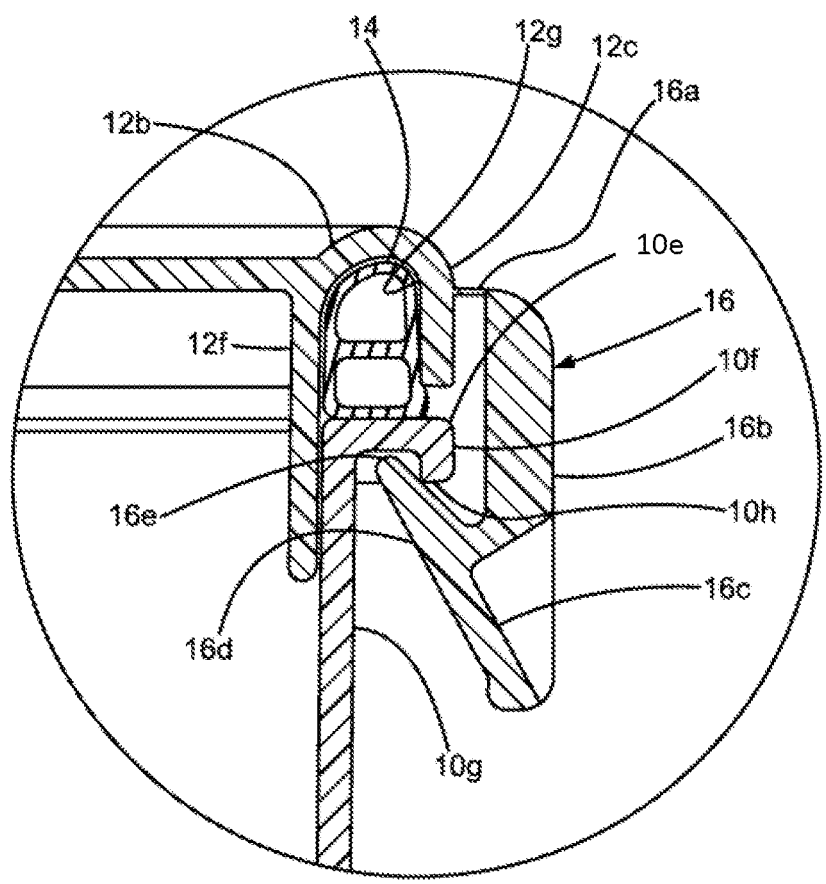
FIG. 6 is a cross-sectional view of a portion of the container wall, skirt, lid, latch and locking tab taken along lines 6 in FIG. 5.
Figure 7:
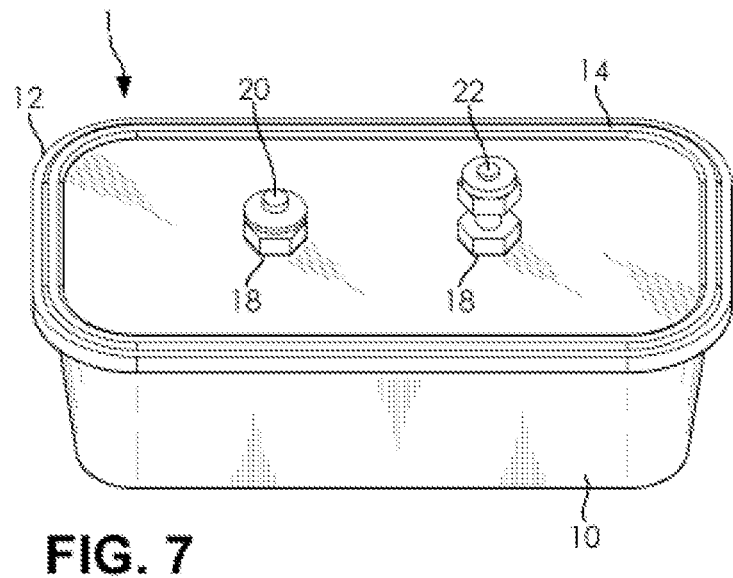
FIG. 7 is a top perspective view of a sealable sampling container according to embodiments of the present invention.

Referring now to the drawings and particularly to FIGS. 1-8, an open top container 1 that has a vessel 10 having a bottom wall 10a, longitudinal and transverse walls 10b and 10c, respectively, which intersect at corners 10d. The walls 10b, 10c extend upwardly to a generally flat peripheral sealing surface 10e (FIG. 2). According to embodiments, the corners 10d are rounded, which aids in cleaning, storing, and transporting the vessel 10. As illustrated in FIG. 6, the sealing surface 10e merges with a down turned flange 10f spaced outwardly from the outer surface 10g of the peripheral walls 10b and 10c. The flange 10f terminates in a free edge 10h, which in cooperation with the lid latches and locking tabs serve to lock the lid 12 in place on the container as will be explained. While the present invention is detailed with respect to a 640 milliliter (ml) container in FIGS. 1-8, it is appreciated that other sizes and shapes of vessels are readily employed with the present invention including sizes that range from 1 to 50,000 ml volumes with appropriately sized valving. Other shapes operative herein include cylindrical, hemispherical, and other polygonal shapes. It should be appreciated that a set of vessels with various volumes can be used to allow a trainee to sample lower partial pressures of a test substance when loaded in the like amounts between vessels of different volumes.

Figure 4:
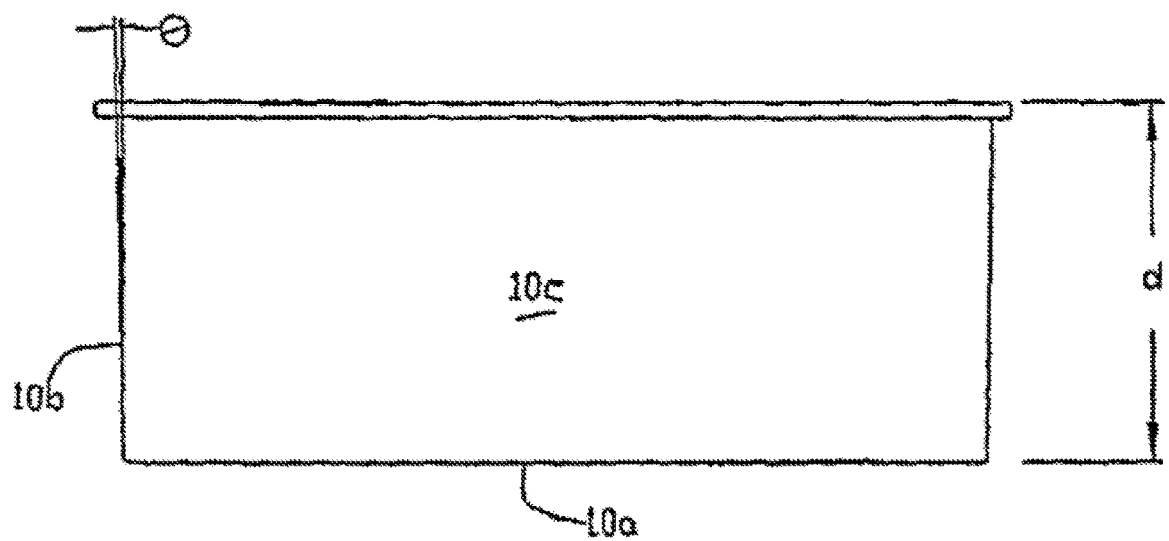
FIG. 4 is a side view of a container of a sealable sampling container according to embodiments of the present invention.
Figure 5:
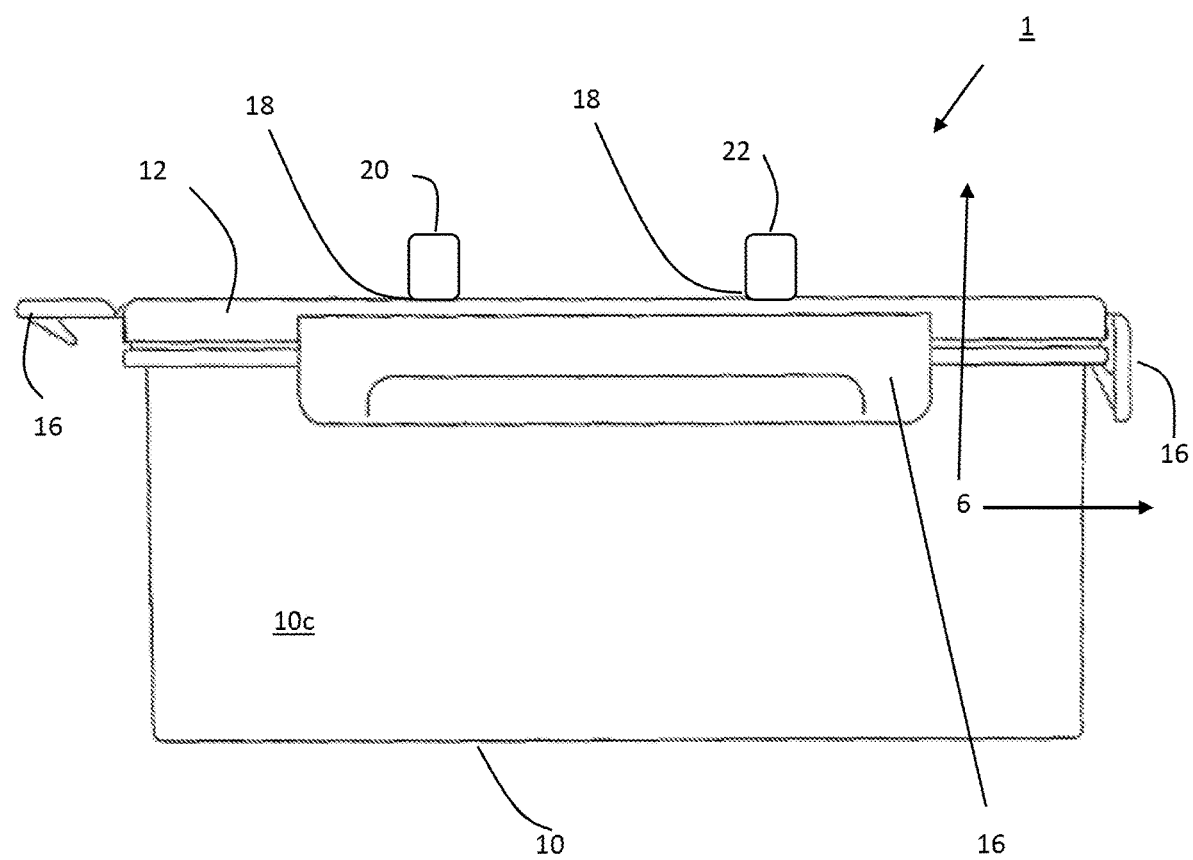
FIG. 5 is a side view of the sealable sampling container of FIG. 1 with the lid positioned on the container and showing a latch handle in the unlocked position (left hand side) and locked position (right hand side)

According to embodiments, the vessel 10 has a square configuration the length l of the longitudinal walls and the width w of the transverse walls have the same dimension. According to other embodiments, the vessel 10 has a rectangular configuration, in which the length, l of the longitudinal walls is greater than the width w of the transverse walls. The depth d of the container 10 may vary depending on the length and width of the walls of the vessel. According to embodiments, the container has a volume of 700 to 1200 ml. According to embodiments, the peripheral walls of the vessel are slanted outwardly at a small angle θ, e.g., 1°-7° depending upon the depth d so that the bottom walls of all containers for each size of opening are the same for stacking purposes as shown in FIG. 4. This angle θ also allows the container to be readily removed from the mold during manufacturing and permits the empty containers of the same size opening to be nested, thereby decreasing the volume required for shipping purposes. In addition, the peripheral walls of the vessel are provided with a slight outward or convex curve to strengthen the peripheral walls and inhibit any inward collapse of the walls. According to embodiments, the vessel 10 is formed of any of plastic, metal, or wood. In some inventive embodiments, the vessel 10 is molded of a suitable plastic such as polypropylene, polyethylene, polyphthalates, polycarbonate, or copolymers thereof in which the majority by subunits by number are any of the aforementioned.

The complementary lid or cover 12, includes a top planar wall section 12a which merges with a short upwardly inclined peripheral section 12b joined to a downwardly extending peripheral skirt 12c having longitudinal and transverse sides 12d and 12e. The lid further includes an inner flange 12f, which with the peripheral skirt 12c, brackets the vessel sealing surface 10d and forms a downwardly facing cavity 12g for removably retaining a gasket 14. The lid inner flange 12f extends below the container sealing surface in the closed position to guide the lid onto the container open top. According to embodiments, the gasket 14 is an elastomeric material that illustratively includes fluoroelastomer, silicone, neoprene, EPDM, silicone, gum rubber, nitrile rubber, Buna-N rubber, and NBR.

According to embodiments, a latch 16 is molded integrally with the lid 12 on each side thereof with a living hinge 16a allowing each latch limited pivotal movement about each hinge line. With reference to FIG. 6, each latch 16 includes a latch handle in the form of an elongated plate 16b with a recessed central section 16c and three inwardly and upwardly extending horizontal locking tabs 16d terminating in a free end 16e which snaps under the free edge 10h of the container flange 10e in the locked position. The latch 16 and locking tabs 16d are generally in the form of a reverse letter J. According to embodiments, the locking tabs 16d, and particularly the surfaces thereof, which contact and slide under the container flange free edge 10h, are formed along a slight curve having the same radius as the curve of the adjacent flange and the container side wall. This curved arrangement and the use of plural locking tabs 16d on each latch 16 allows the locking tabs to be decoupled from the container flange free end. It is appreciated that the present invention allowed for removal of the lid 12 without contact to surfaces that have been exposed to the agent present in the volume of the container 10.

The present invention also includes at least two through holes 18 formed in a wall of the vessel 10 or in the top planar wall section 12a of the lid 12, as shown in the figures. A venting port 20 and a sampling port 22 are affixed within the through holes 18, respectively. According to some inventive embodiments, the venting port 20 comprises a ⅛ inch SWAGELOK® bulkhead union fitting, while the sampling port 22 comprises a ¼ inch SWAGELOK® bulkhead union fitting. Perfluoropolymer tape is used to create a tighter seal around the bulkhead fittings within the through holes 18. Additionally, a ⅛ inch plug and a ¼ SWAGELOK® plug are used to seal the venting and sampling ports, respectively, when not in use with chemical detection equipment. It is appreciated that other conventional gas tight valves are operative herein, such as SWAGELOK® ultra-torr vacuum fittings, VCR® metal gasket face seal fittings, "B" type VCO® l-ring face seal fittings, dielectric fittings, and VCO® O-ring face seal fittings. According to embodiments, the union fittings and associated plugs are formed of stainless steel, perfluoropolymer, alloy 20, 6-cooly, alloy 400, alloy 600, alloy 825, alloy C-276, aluminum, brass, carbon steel, nylon, PFA®, PTFE, alloy 2507®, or titanium.

In use, a trainer removes the lid 12 of the container 1 and inserts tissues or other absorbent media within the vessel 10. Next, the trainer uses a syringe to measure out a known volume of a volatile chemical to dose the tissues within the vessel 10. The tissues may be dosed either while the lid 12 is off, or while the lid 12 is on the container 1 and one of the ports 20, 22 is unplugged. Once the vessel 10 is dosed with the desired chemical, the lid 12 is reattached, both ports 20, 22 are plugged, and the assembled container 1 is set aside until the desired time of training.

Figure 8:
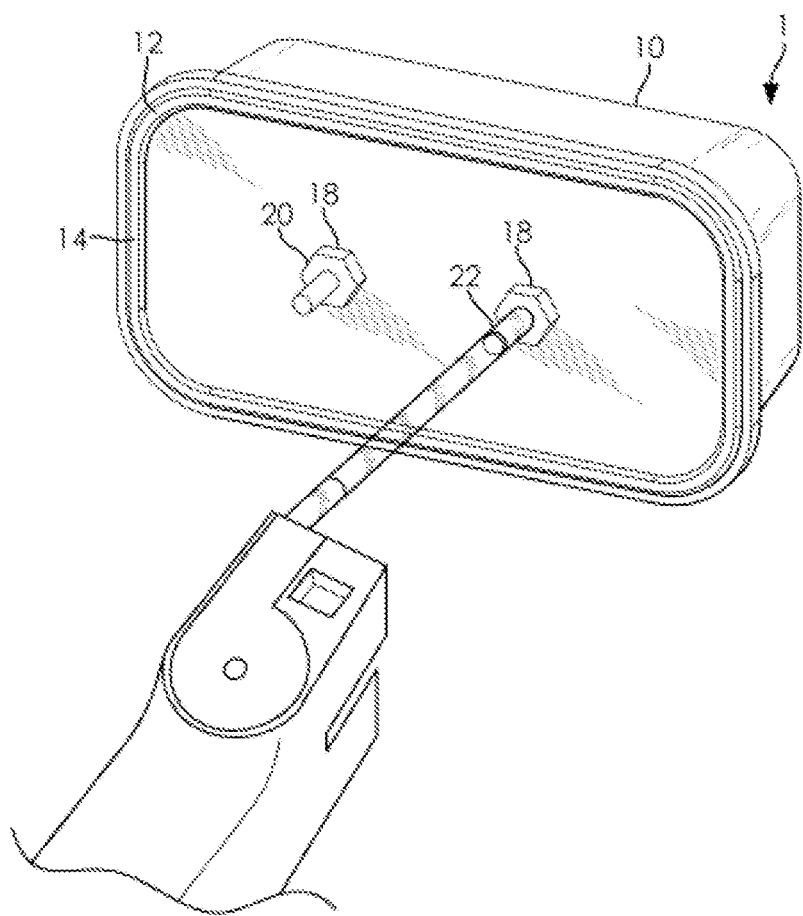
FIG. 8 is a sealable sampling container according to embodiments of the present invention in use with a Draeger Gas Detection Tube chemical detection equipment.

During training, the venting and sampling ports 20, 22 can be unplugged as required depending on the chemical detection equipment being for which training is being conducted. For example, if the chemical detection equipment actively draws in air samples using a pump or fan, the detection equipment can be connected directly to the sampling port 22 and then the venting port 20 will also be opened to prevent a vacuum. When the chemical detection equipment does not create a vacuum the venting port 20 can remain closed. The present invention is used for training of colorimetric chemical detection equipment, such as Draeger Gas Detection Tubes, as shown in FIG. 8, ion mobility spectrometry (IMS)-based chemical detection equipment, such as the Joint Chemical Agent Detector (JCAD), mass spectrometry (MS)-based chemical detection equipment, such as the MX908, as well as other chemical vapor detection equipment.

Accordingly, the present invention provides a method for a trainee of chemical detection equipment to safely sample volatile vapors within any training setting as they are trained on the proper use and operation of chemical detection equipment while minimizing exposure of the user to the vapors contained within the training equipment. The container of the present invention is advantageous in that it is stackable, mobile, sealable, and easy to obtain and transport such that as many as are needed for a training session may be made available. The inventive container is configured to safely contain volatile chemical vapors while minimizing the exposure of a trainee to the vapors within the container. Furthermore, the inventive container allows teaching laboratory personnel to dose the container with a known amount of chemical for sampling purposes and allows a trainee to safely sample the volatile vapor contained in the container. Once training is completed, the invention is easily cleaned of chemical sampling substance and ready for reuse. The invention is suitable for use in a classroom or other than laboratory setting for chemical vapors that pose a minimal health and safety risk to the user. The invention may be used in a non-educational role with any chemical detection technology that requires the sampling of volatile headspace vapors, whether by passive or active sampling through exposure or vacuum technologies for sampling of substances that actually require ventilation hoods or respiratory wear.

Sample can be loaded into the container with something known to create a positive result on the chemical detection equipment. Illustrative of the equipment that can be used to load sample are a syringe or pipette for liquid, a previously weighed amount for solids, or metered gasses. Educational process would be to follow the chemical detection equipment's standard training protocol. By way of example, techniques for collection of a volatile sample for gas chromatography as detailed in de Koning, S., Janssen, H. & Brinkman, U.A.T. Modern Methods of Sample Preparation for GC Analysis. *Chroma* 69, 33 (2009); the contents of which are hereby incorporated by reference.

In a use environment, a known amount of a volatile chemical or material is loaded into an inventive sealable sampling container by teaching laboratory personnel. It is appreciated that multiple containers can be so loaded to provide for a laboratory class experiment. The substances loaded can vary between containers as to concentration, composition, ratio of compositions, or a combination thereof. A container can be presented to a trainee as a known, blind sample, or even a double blind sample relative to the teaching laboratory personnel. The container is given to the trainee outside of a ventilation hood allowing training outside of an overcrowded ventilation hood or laboratory setting. Typically, the trainee is presented with educational training in the form of slides or an educational presentation on the technology and sampling procedure. It is appreciated that this can be done prior to sampling, or after a trainee has attempted intuitive sample collection. The presentation materials in some embodiments include a video or in-person demonstration to the trainee with the inventive sampling container as the sample source. The trainee's attempts to sample a substance from the container are validated in some inventive embodiments by obtaining data from testing instrumentation as to the identity and/or concentration of the sample relative to that loaded into the container. As a result, a feedback mechanism is created as to trainee sampling technique.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A sealable sampling container for use with chemical detection equipment, comprising:
   an open top vessel having a bottom and a plurality of walls upwardly extending therefrom and terminating in a sealing surface, the bottom and the plurality of walls defining a volume within said open top container, and wherein the sealing surface of said vessel merges with a down turned flange that is spaced outwardly from an outer surface of each of the plurality of walls;
   a gasket configured to engage with the sealing surface of said vessel;
   a lid configured to engage with said gasket at the sealing surface and lock to said vessel, wherein said lid includes a plurality of latches positioned around the perimeter thereof, and wherein each of said latches is pivotally connected to said lid and includes one or more locking tabs for snapping under a free edge of the down turned flange of said vessel; and
   a sampling port affixed to one side of said vessel or said lid, said sampling port providing fluid communication between the volume within said vessel and an external environment, and
   wherein said sampling container is configured to safely contain chemical vapors when said sampling port is sealed and to release the chemical vapors when unsealed so that said chemical detection equipment can be exposed to the chemical vapors for training or testing purposes.

2. The sealable sampling container of claim 1, wherein the plurality of walls intersect at rounded corners.

3. The sealable sampling container of claim 1, wherein the volume is 700 to 1200 ml.

4. The sealable sampling container of claim 1, wherein the plurality of walls of said vessel are slanted outwardly from the bottom toward the sealing surface.

5. The sealable sampling container of claim 1, wherein said vessel and lid are formed of any of plastic, metal, or wood.

6. The sealable sampling container of claim 1, wherein said vessel and lid are molded of polypropylene, polyethylene, polyphthalates, polycarbonate, or copolymers thereof in which the majority by subunits by number are any of the aforementioned.

7. The sealable sampling container of claim 1, wherein said gasket is a silicone, rubber or polymer gasket material.

8. The sealable sampling container of claim 1, wherein said vessel and lid are molded of a suitable plastic such as polypropylene, polyethylene, or other suitable polymers.

9. The sealable sampling container of claim 1, wherein said sampling port includes a ¼ inch bulkhead union fitting.

10. The sealable sampling container of claim 1, further comprising a sampling port plug that is configured to seal said sampling port.

11. The sealable sampling container of claim 1, further comprising a venting port affixed to one side of said vessel or said lid, said venting port providing fluid communication between the volume within said open top container and the external environment.

12. The sealable sampling container of claim 11, wherein said venting port includes a ⅛ inch bulkhead union fitting.

13. The sealable sampling container of claim 11, further comprising a venting port plug that is configured to seal said venting port.

14. A method of training a person in the proper use of chemical detection equipment, the method comprising:
provided the person being trained with the sealable sampling container of claim 1, wherein said container has been dosed with a desired chemical sample and sealed;
having the trainee unseal the container and release the chemical sample for use with chemical detection equipment for training purposes; and
wherein the container is configured to safely contain volatile chemical vapors to minimize exposure of the person being trained to the chemical vapors within the container and to safely release the chemical vapors only when required so that the training can be conducted without the use of ventilation hoods or the use of respiratory protection equipment.

15. The method of claim 14, further comprising educating the trainee as to the proper steps for releasing and transferring the sample to the chemical detection equipment and obtaining data from the chemical detection equipment as to the identity and/or concentration of the sample relative to the substance in said container.

16. The method of claim 14, further comprising teaching the trainee how to properly dose the container with a known amount of chemical for sampling purposes.

17. The method of claim 16, wherein the trainee places adsorbent media in the container and measures out and doses the absorbent media with a known amount of chemical.

\* \* \* \* \*